United States Patent [19]
Walters

[11] Patent Number: 5,791,334
[45] Date of Patent: Aug. 11, 1998

[54] HEAT PACK RESISTANT TO SADDLE-BAGGING

[75] Inventor: Dale E. Walters, St. Louis, Mo.

[73] Assignee: Omni Therm, Inc., St. Louis, Mo.

[21] Appl. No.: 617,113

[22] Filed: Mar. 18, 1996

[51] Int. Cl.$^6$ ..................................... F24J 1/00
[52] U.S. Cl. .................. 126/263.03; 126/263.01; 126/263.07; 126/204; 126/205
[58] Field of Search .................. 126/205, 204, 126/263.01, 263.03, 263.07; 165/46

[56] References Cited

U.S. PATENT DOCUMENTS

| | | | |
|---|---|---|---|
| 3,950,158 | 4/1976 | Gossett | 62/4 |
| 5,143,048 | 9/1992 | Cheney, III | 126/263.04 |
| 5,184,613 | 2/1993 | Mintz | 607/104 |
| 5,339,796 | 8/1994 | Manker | 126/263.03 |

*Primary Examiner*—Larry Jones
*Attorney, Agent, or Firm*—Kalish & Gilster

[57] ABSTRACT

A heat pack for use as a warmer mattress for infants is formed of a flexible container at least partly filled with a supercooled aqueous salt solution which is selectively trigger-activated to produce heat by exothermic crystallization. The container is compartmentalized, being divided into several compartments by a heat-sealing arrangement of upper and lower joined halves. When crystallization is initiated by activating the trigger, crystallization is propagated quickly into the several compartments, from each of which heat is thereby liberated, the compartments being shaped such that the crystallizing solution in each compartment is effectively trapped therein to substantially prevent saddle-bagging, and whereby the heat pack reliably and safely supports an infant upon the warmer mattress. The upper and lower halves are heat-sealed together in various possible heat seal patterns defining the compartments, as by sealed margins and heat-seal extensions extending inwardly from the peripherally margins. The triggering arrangement disclosed includes opposed puncturing devices under a sealing arrangement, incorporated crystals of the salt of the solution on the puncturing devices, which may be mutually squeezed together for causing puncturing of at least one side of the container for triggering. As a warmer mattress, the heat pack provides a gentle, warm, supportive non-saddle-bagging infant support surface, for use in medical institutions to support neonatal infants or otherwise when they are placed upon a surface for examination and care.

16 Claims, 6 Drawing Sheets

HEAT PACK RESISTANT TO SADDLE-BAGGING

BACKGROUND OF THE INVENTION

1. Field of the Invention

This invention relates to heat packs, and more particularly to such a heat pack as in the form of a warmer mattress for infants, having a flexible, compartmentalized container having a supercooled aqueous salt solution which can be activated by a trigger to produce heat. The compartmentalized arrangement effectively traps therein crystallizing solution to substantially prevent saddle-bagging and reliably and safely support an infant upon the warmer mattress.

2. Related Art

Heretofore, it has been proposed to employ thickening agents such as hydroxyethylcellulose (HEC) in the salt solution or to submerge a foam pad, as of cellulosic material, in the container to alleviate the problem of saddle-bagging when the heat pack is in the form of a pad is applied to the human body, or where it constitutes an infant warmer mattress, when an infant is placed thereon. By saddle-bagging is meant the displacement of the crystallizing or crystallized solution such that undesirable lesser quantities of it are present from the areas of the device from which it is displaced and undesirable greater quantities of it accumulate, as in opposite marginal extremes, as if mimicking the effect of a saddle-bag to drape to opposite sides of an animal's back, so that the pad or mattress is too thick in some areas and too thin in others.

SUMMARY OF THE INVENTION

A heat pack as herein disclosed is in the form of an advantageous warmer mattress for infants, although in the broader sense it is a heat pack, such as capable for many other therapeutic uses, as in warming parts of the body, or capable for as a stadium heater. The warmer mattress being at least partly filled with a supercooled aqueous salt solution, preferably sodium acetate salt aqueous solution, which can be activated by a trigger to produce heat.

The mattress containing the solution forms a bag-like flexible container, and the trigger is affixed to the flexible container. The container is divided by heat-sealing of upper and lower component halves into a series of pockets, each being essentially U-shaped if viewed in plan, so that the container is effectively compartmentalized. Thus, even though divided into several compartments or what may be termed confinement regions are volumes, all of the compartments form but extensions of the overall volume of the solution. Because they are interconnected in this way, forming parts of the whole, when solution is triggered precipitation, or what is referred to herein as crystallization, is initiated effectively throughout the container, as crystallization proceeds and propagates quickly into the several compartments, from each of which heat is thereby liberated. The compartments or pockets are such that the crystallizing solution in each compartment is effectively trapped or at least confined in a relative sense therein, such that solution will not be forced as it otherwise would to opposite ends of the mattress. This substantially prevents saddle-bagging, so otherwise typical especially when the salt solution has not been thickened, for which reason there has long proposed the addition of stiffeners or extrinsic materials into the solution, such as thickeners (an example being HEC, known for many years as suitable for thickening such a solution) to allay saddle-bagging. With the new construction, it is now found that saddle-bagging is effectively no longer a problem, even if the solution in the new mattress is not thickened. Because no thickener need be employed, economy and simplicity are provided.

The advantageous compartmentalization is carried out by applying a heat-sealing pattern wherein heat seal extensions of parallel, intersecting, staggered or chevron configuration are used. According to one mode, the extensions may run lengthwise of the container to impede lateral displacement of the solution when triggered, or they may extend in lateral relationship to the longitudinal axis of the container, to impede lengthwise solution displacement; and indeed, a combination of lengthwise and lateral heat seal extensions (which demarcate and define the compartments) may be employed to possible advantage. According to some advantageous embodiments, the heat seal extensions effectively define a serpentine relationship of the interconnected compartments, so that the overall volume of solution extends along a major dimension of the device in serpentine fashion.

As a benefit of the compartmentalized configuration, the new warmer mattress more reliably and safely supports an infant, for example, upon the warmer mattress. Therefore, its preferred mode as a warmer mattress for infants, the new heat pack provides a gentle, warm, supportive non-saddle-bagging infant support surface, for use in medical institutions to support neonatal infants or otherwise when they are placed upon a surface for examination and care.

Moreover, the preferred construction employs materials permitting the entirety of the mattress to be prepackaged in a sterile condition for immediate safe use in medical environments, and then safely disposed after use for reasons of economy and safety, without risk of introducing ecologically or environmentally deleterious materials. Thus, the new construction makes possible warmer mattresses and other therapeutic heat pads which do not contemplate any re-usability.

The triggering arrangement proposed employs at least one puncturing means, but preferably a pair of puncturing devices disposed on opposite faces of the flexible container, and covered by a sheet of sealing material adhesively or otherwise sealed to the container material, and sealing against loss of the solution upon puncturing of the container by the puncturing means. Each such puncturing device may have one or more projections which produce a small puncture in the container material, admitting minute quantities of air for initiating crystallization, but according to a most preferred inventive configuration, the puncturing device projections each are coated with dry crystals of the material constituting the salt solution, the dry crystals initiating or at least enhancing the crystallization, by permitting the salt solution to contact the salt crystals upon said puncturing.

Other objects or advantages will be apparent or are pointed out in the following description.

BRIEF DESCRIPTION OF DRAWINGS

Corresponding reference characters identify corresponding elements throughout the several views of the drawings.

DESCRIPTION OF INVENTIVE EMBODIMENTS

Figure 1:
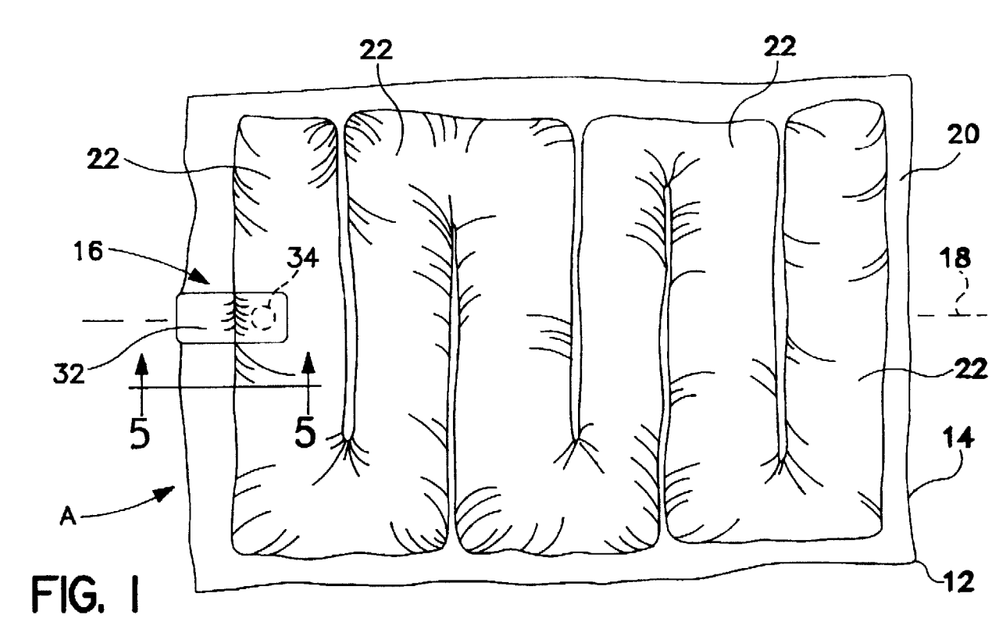
FIG. 1 is plan view of a warmer mattress in accordance with and embodying the present invention.

Referring to the drawings, FIG. 1 illustrates a heat pack generally designated 12 in the form of a warmer mattress for infants. Herein referred to as warmer mattress embodiment A, it includes a bag- or pillow-like flexible container 14 at least partly filled with a supercooled aqueous salt solution, namely sodium acetate, which can be activated by a trigger assembly generally designated 16 to produce heat. The trigger assembly is affixed to the flexible container externally thereof. An internal trigger of known type may instead be used, without providing the advantages of the present trigger assembly, which is described below.

Container 14 is compartmentalized, being divided into several compartments, which are interconnected so that, when crystallization is initiated by activating the trigger, crystallization is propagated quickly into the several compartments, from each of which heat is thereby liberated. Trigger assembly 16 is located at one end of container 14, which is rectangular and of sufficient length readily to accommodate an infant lying generally along the horizontal axis 18.

Figure 2:
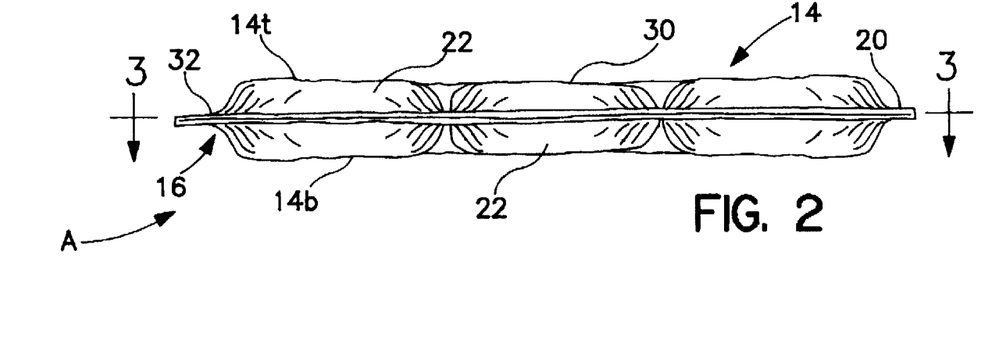
FIG. 2 is a side elevation view of the warmer mattress of FIG. 1.
Figures 3, 4, 5:
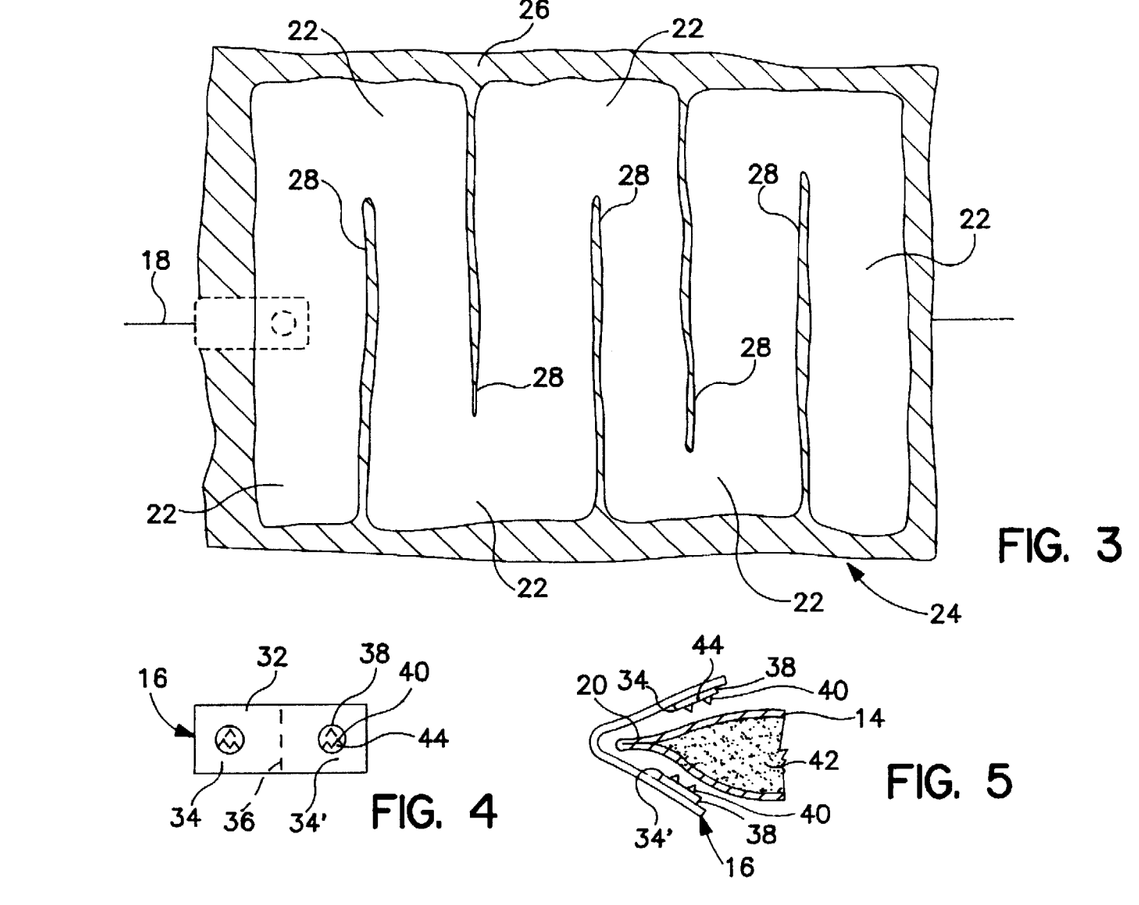
FIG. 3 is a horizontal cross-section taken along line 3—3 of FIG. 2.
FIG. 4 is a plan view of a trigger assembly of the warmer mattress of FIG. 1.
FIG. 5 is a partial vertical cross-section taken along line 5—5 of FIG. 1, with trigger assembly elements shown separated for clarity in further illustrating it.

Referring to FIG. 2, container 14 has top and bottom halves 14t,14b which are of resilient, heat-sealable material and which accordingly are heat-sealed together, providing a peripheral flange 20 defining the outer margins of container 14 and within which there are seen to be what are effectively a plurality of individual pillowed compartments 22 but which are virtually constituted by single chamber of serpentine configuration defined by a heat-sealing pattern generally designated 24 formed by a zig-zag line of seal of intermeshed configuration as seen in FIG. 3.

In FIG. 3 it will be understood that peripheral heat-sealing provides a peripheral seal margin 26 from which inwardly extend generally rectilinear extensions 28 which are in staggered intermeshed configuration along the horizontal axis 18, there being in this example three such extensions inwardly from each side so as to provide effectively six compartments 22. As heat-sealing pattern 24 of FIG. 3 reveals, each adjacent pair of compartment 22 bridges at the distal ends of extensions 28 in U-defining configuration so that, if one arbitrarily considers the pattern symmetrically as two halves relative to horizontal axis 18 one may treat the bridged pairs of compartments as effectively being two opposed pairs three U-shaped chambers or confinement regions, the significance of which will become still more apparent as the description continues.

Preferably, the material of which container 14 is formed is a nylon-based fabric-backed polymeric laminate material of thickness of preferably between 2 and 5 mil and most preferably about 4 mil, such material being available from the DuPont Chemical Company and sold under the trademark "BIAX."

The foregoing material is oriented so as to provide an infant-receiving upper surface 30 (FIG. 2) of soft, textured character comfortable to an infant. The new warmer mattress 12 is to be used in institutions and other locations for providing a gentle, warm, supportive non-saddle-bagging infant support surface, as in medical institutions and facilities such as clinics, treatment offices and physician's offices, to support neonatal infants or otherwise when they are placed upon a surface for examination and care. Thus, it will be understood that warmer mattress 12 is to be selectively triggered for providing its warming action by initiation of crystallization by manipulation of trigger assembly 16.

Container 14 is at least partly filled with a supercooled salt solution in accordance with co-assigned U.S. Pat. No. 5,305,733, which is herein incorporated by reference.

Referring now also to FIGS. 4 and 5, trigger assembly 16 is formed from a flat rectangular sheet 32, namely most preferably a tape of polymeric sheet material. To tape 32 are affixed as by adhesive two piercing elements 34,34' and which sheet is then folded along a fold line 36 and wrapped about peripheral flange 20 for heat-sealing or adhesive securement with the two piercing elements 34, 34' in contact with opposite outer surfaces of container 14. Such piercing or puncturing elements may be constructed in accordance with above-referenced U.S. Pat. No. 5,305,733 which discloses a trigger for such a heat pack as the present, and wherein the piercing element or elements of the trigger will allow a minute quantity of air to be admitted interiorly of the container, initiating crystallization of the salt solution, and causing the pack to exotherm. Generally, as therein disclosed, and as revealed by FIG. 5, puncturing or piercing means or elements 34,34' may each be formed of a thin metal base plate 38 having one or more upstanding piercing members 40 protruding therefrom, as by being constituted by upset portions of the metal base plate.

In accordance with the preferred construction here employed, the triggering means employs tape 32 as a sealing means, secured most preferably by contact adhesive seal, and dimensions greater than the base plate 38. As plates 38 are on the opposite sides of the flexible container, a single length of tape 32 covers both by being wrapped about the bag margin, serving also to attach piercing elements 34, 34' to the container exterior. Moreover, the sealing means 32 prevents any leakage of the solution from the container when the container is punctured by either trigger.

As shown in FIG. 5, wherein the elements of piercing unit 16 are separated from the relevant proximate portions of container 14 for clarity of illustration and as approximating the assembly during manufacture, the salt solution is designated 42. Its crystallization can be initiated either or both of piercing elements 34,34' puncturing the bag, so that at least minute amounts of air may enter the container in the locality of the resulting pierce, without any substantial loss of liquid from the container, and causing the crystallization to proceed. Tape 32, being tightly adhered to container 14, does not permit loss of liquid from the container. As a definitive improvement of the piercing elements 34,34' it is preferred to apply a drop of sodium acetate at 44, being after application remaining as a bit of dry sodium acetate. Thus, upon piercing, the drop 44 of dry sodium acetate effectively seeds the crystallization, so that it is initiated even more quickly. Moreover, the drop 44 of dry material is protected by the tightly adhered tape 32.

In operation, crystallization of sodium acetate solution 42, proceeds upon manual application of squeezing pressure on opposite sides of the trigger assembly 16, causing either or both of piercing elements 34,34' to puncture the bag, so that at least minute amounts of air may enter the container in the locality of the resulting pierce, and with seeding by the dry sodium acetate drop 44, as applied to either or both piercing element 34,34', causes crystallization to proceed at once.

During such actuation of the heat pack and resultant crystallization, the triggering propagates rapidly throughout the contents of warmer mattress 12, following the serpentine path evident in FIG. 1, so that promptly after triggering, crystallization is underway throughout the sodium acetate salt solution, and continues for a number of minutes, the exothermic conversion producing a gentle warming of the surface of warmer mattress 12, for example, about 110° F.

Figures 6, 10:
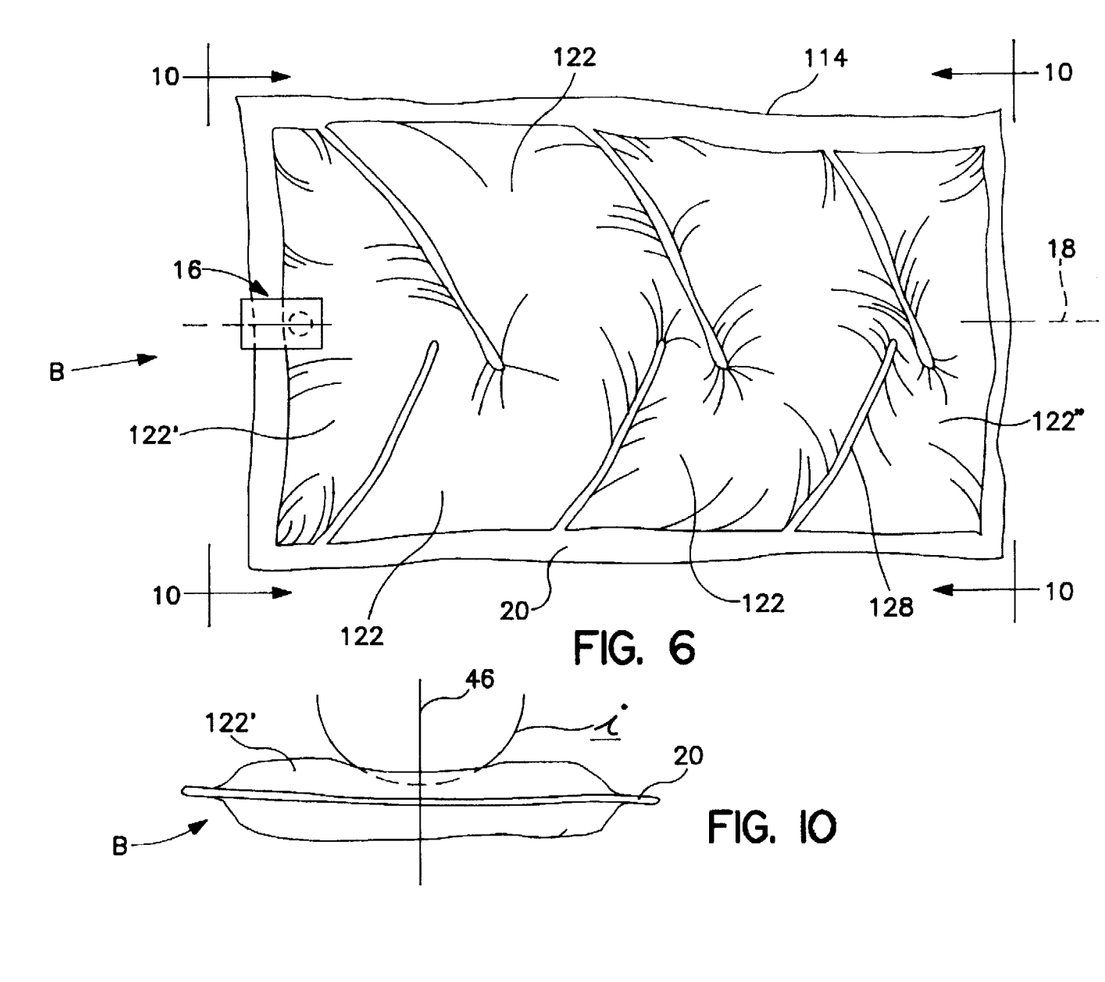
FIG. 6 is a plan view of a second warmer mattress embodiment in accordance with and embodying the present invention.
FIG. 10 is an end elevation view of the warmer mattress of FIG. 10, as illustrative of the use of any warmer mattress embodiment in supporting an infant.
Figure 7:
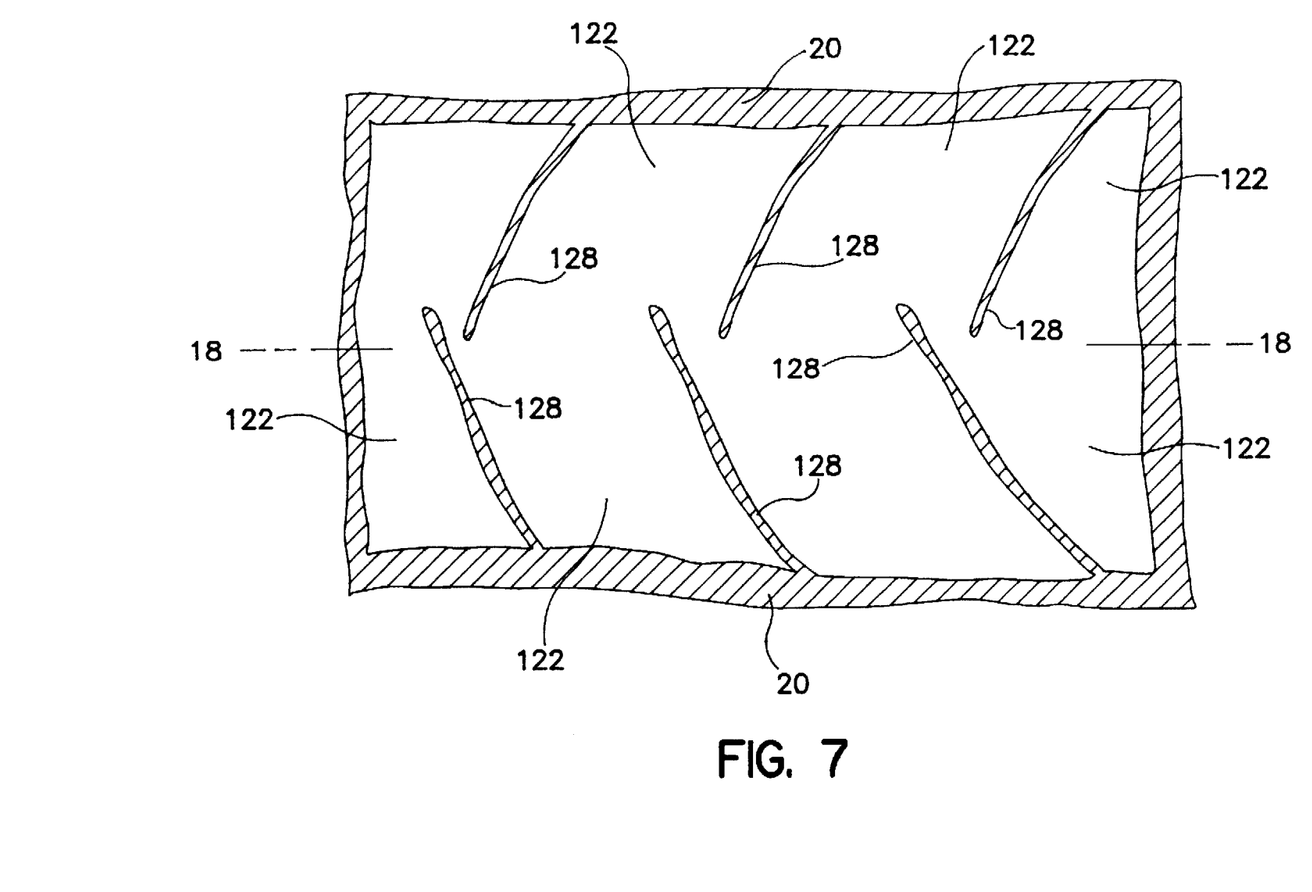
FIG. 7 is a side elevation view of the warmer mattress of FIG. 6.

Referring to FIG. 6, a second embodiment B comprises a compartmentalized container 114 divided into several interconnected compartments 122 which are symmetric about horizontal axis 18, but defined and separated by a heat-sealing pattern generally designated 124 formed of a chevron pattern of staggered intermeshed elements shown in FIG. 7 as being approximately rectilinear extensions 128 which are in staggered intermeshed configuration along the horizontal axis 18, there being again in this embodiment three such extensions inwardly from each side of peripheral seal 20 in generally U-defining arrangement as in the case of embodiment A so as to provide again effectively six such compartments 122 but end compartments 122' and 122" of which being smaller than four main compartments. Thus, it is understood that by selection of a chevron pattern as indicated, variation in the side of the individual compartments defined or divided by the extensions 128 has been achieved, and for reasons which will be further understood in the following description.

As FIG. 7 similarly reveals, the distal ends of extensions 128 provide U-defining configuration of the compartments, though offset and canted, so that, again one may consider that the pattern provides a degree of symmetry in two halves relative to horizontal axis 18, and comparably to embodiment A. Further, it is seen that heat-seal extensions 128 can be slightly curved or irregular or arcuate.

Figure 8:
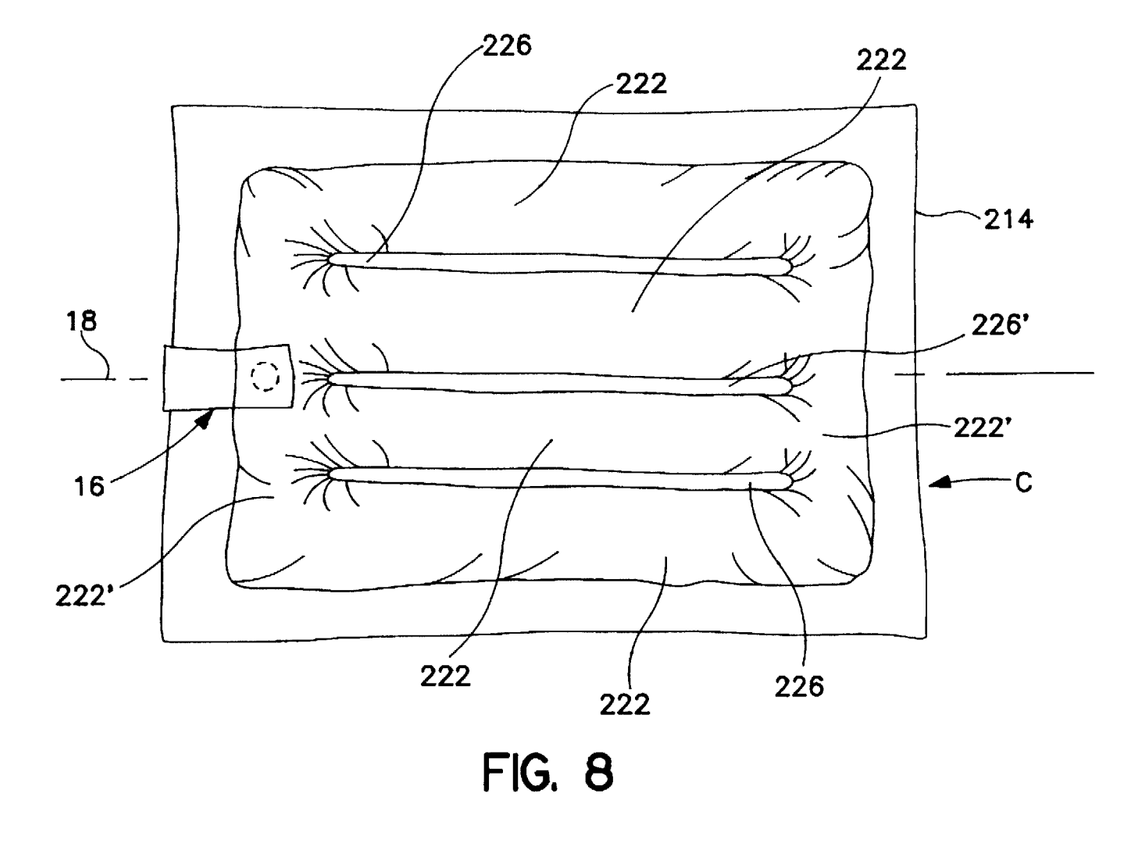
FIG. 8 is a plan view of a third warmer mattress embodiment in accordance with and embodying the present invention.
Figure 9:
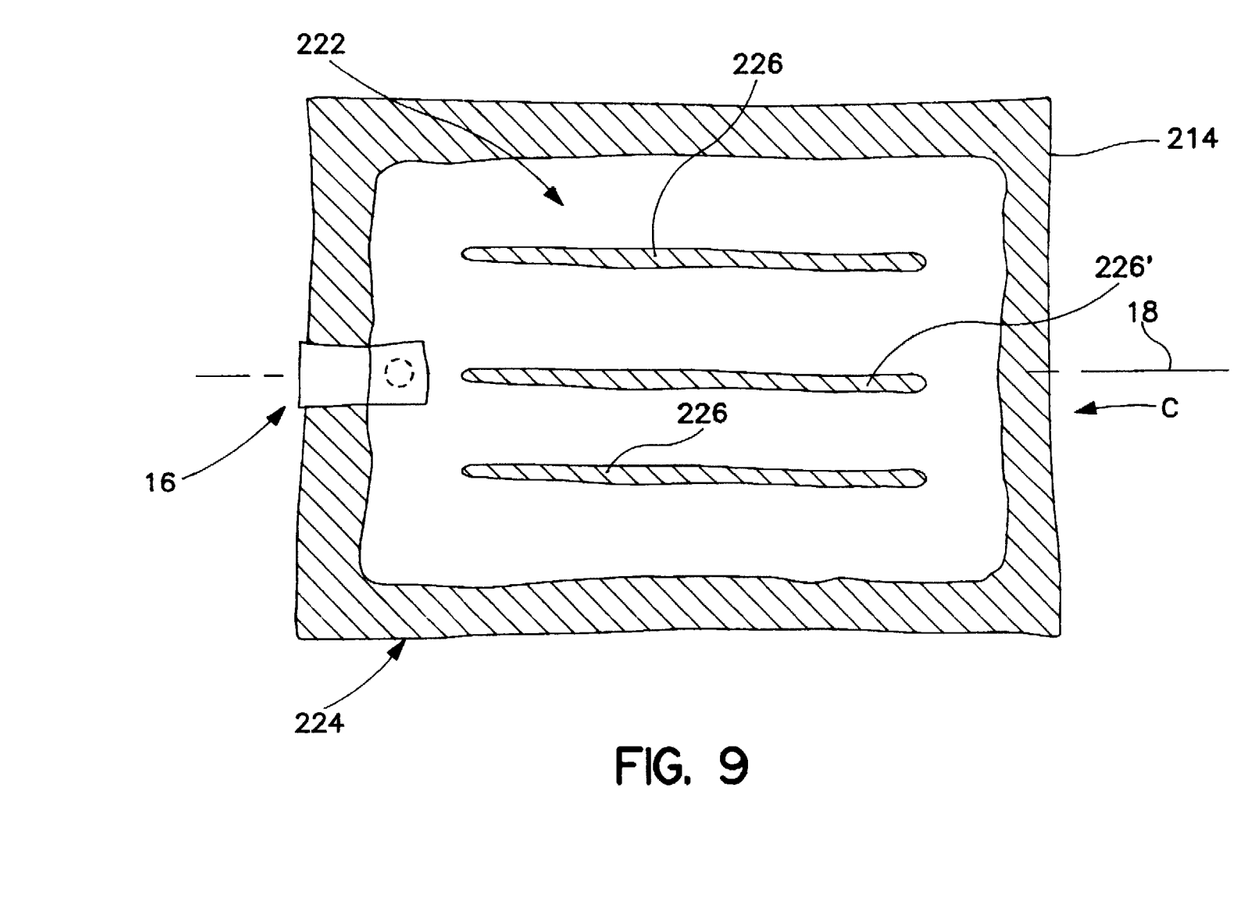
FIG. 9 is a side elevation view of the warmer mattress of FIG. 8.

FIGS. 8 and 9 demonstrate yet another embodiment C comprises a compartmentalized container 214 divided into multiple interconnected compartments 222 which are symmetric arranged in lengthwise pairs about horizontal axis 18, being defined and separated by a heat-sealing pattern generally designated 224 formed of a by a substantially parallel pattern of elongate, rectilinear seal lines or extensions 226 shown in FIG. 9 as arranged in a pattern of three, one of which 226' extends along the horizontal axis 18, and the other two being spacedly located outwardly from extension 226' in essentially or at least partly or generally parallel relationship over a portion of their relative lengths so as to define effectively four main longitudinal compartments 222 but two end compartments 222' of shorter extent than the main compartments.

This is not to say, however, that the two outer seal extensions 222 must be mutually parallel as well as parallel with the centerline extension 222'. For, instead, the several elongate extensions may relatively tend to converge or diverge at different locations along the general length of container 224, or otherwise be varied in their relative spacing and alignment such that the longitudinal compartments may not necessarily be of fixedly constant or precise cross-section or transverse dimension along the entirety of their lengths. Thus, the compartments may instead be varied in accordance with the preferences generally now apparent, which is essentially to confine if not trap the sodium acetate salt solution as it crystallizes once having been triggered. In that way saddle-bagging will be greatly minimized if not eliminated so that an infant may be more reliably and assuredly supported in a warm and stable location upon the warmer mattress of the invention throughout the several minutes during which the exotherm continues.

When the triggering means 16 of any of embodiments A, B or C is selectively actuated, by squeezing the opposed triggering elements toward each other, a crystallization of the sodium acetate salt solution is at once initiated, and proceeds quite rapidly along the length and width of the warmer mattress, and yet is an orderly process which occurs throughout the solution and requires some minutes to be fully completed, during which the exothermic change of state provides an assured, gentle warming effect and mild temperature increase most suitable for comfortable support of an infant.

The compartments as 22, 122, 222 for embodiments A, B, C, respectively, are such that the crystallizing solution in each compartment is effectively trapped or confined therein or otherwise impeded from flowing from the compartment in order to substantially prevent saddle-bagging, and thus reliably and safely support an infant, for example, upon the warmer mattress.

The general advantages and principles are further understood from FIG. 10 where an infant i is placed upon warmer mattress B, as typifying the use of any of the new warmer mattresses for supporting and warming an infant. The weight of the infant, centered along a central vertical plane 46 tends to urge the crystallizing solution with the warmer mattress towards its peripheral edges 20 and thus away from longitudinal axis 18 (FIG. 6). Thus a displacement of the still fluid but thickening sodium acetate salt solution urges it into the U-shaped compartment regions, as in the case of embodiments A and B, and against the rectilinear seal lines or extensions 228 shown in FIG. 9 for embodiment C, and so tending to avoid a deleterious major displacement of the solution toward the opposite ends of the warmer mattress as would provide an undesirable saddle-bagging tendency.

Although the warmer mattress container is most preferably formed of the above-described material, it may instead be formed of other possibly suitable materials, such as instead being selected flexible container comprising material selected from the group consisting of rubber, vinyl, vinyl coated fabric, polyethylene, or nylon polylaminate other than that identified.

Similarly, other solutions may be employed than identified above, being for example selected from the group consisting of sodium acetate, lead acetate, calcium nitrate tetrahydrate, sodium pyrophosphate and sodium thiosulfate.

In view of the foregoing description of the present invention and various embodiments and methods it will be seen that the several objects of the invention are achieved and other advantages are attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting.

What is claimed is:

1. A heat pack for use as a warmer mattress for infants, comprising a flexible container at least partly filled with a supercooled aqueous salt solution which can be activated to produce heat, triggering means associated with the container for selective actuation to cause the supercooled aqueous salt solution to undergo an exothermic crystallization the container being compartmentalized by being divided into several compartments, which are interconnected so that, when crystallization is initiated by activating the trigger, crystallization is propagated quickly into the several compartments, from each of which heat is thereby liberated, the compartments being shaped such that the crystallizing solution in each compartment is effectively trapped therein to substantially prevent saddle-bagging, the container being formed of a polymeric laminate cloth-covered nylon material, whereby the heat pack may reliably and safely support an infant upon the warmer mattress, and the material provides gentle, soft, and textured character when it comes into contact with the infant.

2. A heat pack as set forth in claim 1 wherein the container is formed of upper and lower halves heat-sealed together by a heat seal pattern defining the compartments.

3. A heat pack for use as a warmer mattress for infants, comprising a flexible container at least partly filled with a supercooled aqueous salt solution which can be activated to produce heat, triggering means associated with the container for selective actuation to cause the supercooled aqueous salt solution to undergo an exothermic crystallization the container being compartmentalized by being divided into several compartments, which are interconnected so that, when crystallization is initiated by activating the trigger, crystallization is propagated quickly into the several compartments, from each of which heat is thereby liberated, the compartments being shaped such that the crystallizing solution in each compartment is effectively trapped therein to substantially prevent saddle-bagging, whereby the heat pack may reliably and safely support an infant upon the warmer mattress, wherein the container is formed of upper and lower halves heat-sealed together by a heat seal pattern defining the compartments, and wherein the heat seal pattern is defined by peripherally sealed margins and by extensions extending inwardly from the peripheral margins, the extensions defining the compartments.

4. A heat pack as set forth in claim 3 wherein the extensions define with the peripherally sealed U-shaped regions of the compartments in which the salt solution will effectively be trapped during its crystallization.

5. A heat pack as set forth in claim 3 wherein the heat seal pattern is defined by peripherally sealed margins and by extensions extending in spaced relation from the peripherally margins, the extensions defining the compartments.

6. A heat pack as set forth in claim 5 wherein the heat seal extensions extending are generally parallel to a horizontal axis of the container.

7. A heat pack as set forth in claim 3 wherein the extensions are in staggered intermeshed configuration along a horizontal axis of the container.

8. A heat pack as set forth in claim 7 wherein the heat seal pattern is defined by peripherally sealed margins and there are a plurality of such extensions inwardly from each side of the container in generally U-defining arrangement, so as to define a corresponding multiplicity of compartments on each side of the horizontal axis.

9. A heat pack as set forth in claim 7 wherein the extensions are generally at angles to the horizontal axis.

10. A heat pack as set forth in claim 7 wherein the extensions are at angles to the horizontal axis, and define a chevron pattern.

11. A heat pack as set forth in claim 3 wherein the salt solution is formed of a salt selected from the group consisting of sodium acetate, lead acetate, calcium nitrate tetrahydrate, sodium pyrophosphate and sodium thiosulfate.

12. A heat pack as set forth in claim 3 wherein the flexible container composes materials selected from the group consisting of rubber, vinyl, vinyl coated fabric, nylon polylaminate and polyethylene.

13. A heat pack for use as a warmer mattress for infants, comprising a flexible container at least partly filled with a supercooled aqueous salt solution which can be activated to produce heat, triggering means associated with the container for selective actuation to cause the supercooled aqueous salt solution to undergo an exothermic crystallization the container being compartmentalized by being divided into several compartments, which are interconnected so that, when crystallization is initiated by activating the trigger, crystallization is propagated quickly into the several compartments, from each of which heat is thereby liberated, the compartments being shaped such that the crystallizing solution in each compartment is effectively trapped therein to substantially prevent saddle-bagging, whereby the heat pack may reliably and safely support an infant upon the warmer mattress, wherein the triggering means comprises at least one puncturing means, and sealing means covering the puncturing means, the sealing means attaching the puncturing means to the exterior of the flexible container, and sealing against loss of the solution upon puncturing of the container by the puncturing means, and wherein the triggering means, when activated, includes opposed puncturing devices which may be mutually squeezed together for causing puncturing of at least one side of the container for triggering.

14. A heat pack as set forth in claim 13 wherein the puncturing devices each can admits a minute quantity of air to the solution for initiating crystallization.

15. A heat pack as set forth in claim 14 wherein the puncturing devices have sharp elements for puncturing the flexible container.

16. A heat pack as set forth in claim 15 wherein the puncturing devices each are coated with dry crystals of the material constituting the salt solution, the dry crystals initiating or at least enhancing the crystallization, by permitting the salt solution to contact the salt crystals upon said puncturing.

* * * * *